(12) United States Patent
Utashima et al.

(10) Patent No.: US 9,040,257 B2
(45) Date of Patent: May 26, 2015

(54) BASIDIOMYCETOUS YEAST MUTANT

(71) Applicants: TOYOBO CO., LTD., Osaka-shi, Osaka (JP); NATIONAL RESEARCH INSTITUTE OF BREWING, Higashihiroshima-shi, Hiroshima (JP)

(72) Inventors: Yuu Utashima, Tsuruga (JP); Takahide Kishimoto, Tsuruga (JP); Shusaku Yanagidani, Tsuruga (JP); Kazuo Masaki, Higashihiroshima (JP)

(73) Assignees: TOYOBO CO., LTD., Osaka-shi (JP); NATIONAL RESEARCH INSTITUTE OF BREWING, Higashihiroshima-shi (JP)

(*) Notice: Subject to any disclaimer, the term of this patent is extended or adjusted under 35 U.S.C. 154(b) by 0 days.

(21) Appl. No.: 14/394,691

(22) PCT Filed: Apr. 23, 2013

(86) PCT No.: PCT/JP2013/061829
§ 371 (c)(1),
(2) Date: Oct. 15, 2014

(87) PCT Pub. No.: WO2013/172154
PCT Pub. Date: Nov. 21, 2013

(65) Prior Publication Data
US 2015/0072379 A1 Mar. 12, 2015

(30) Foreign Application Priority Data

May 17, 2012 (JP) .................. 2012-113449

(51) Int. Cl.
| C12P 21/02 | (2006.01) |
| C12N 1/16 | (2006.01) |
| C12R 1/645 | (2006.01) |
| C12P 21/00 | (2006.01) |

(52) U.S. Cl.
CPC . *C12N 1/16* (2013.01); *C12P 21/02* (2013.01); *C12R 1/645* (2013.01); *C12P 21/00* (2013.01)

(58) Field of Classification Search
None
See application file for complete search history.

(56) References Cited

U.S. PATENT DOCUMENTS

2006/0148049 A1* 7/2006 Fukuchi et al. ............... 435/135

FOREIGN PATENT DOCUMENTS

JP 2012-183012 A 9/2012

OTHER PUBLICATIONS

Masaki, K. et al., "Construction of a new recombinant protein expression system in the basidiomycetous yeast *Cryptococcus* sp. strain S-2 and enhancement of the production of a cutinase-like enzyme.", Appl. Microbiol Biotechnol, Feb. 2012, vol. 93, No. 4, pp. 1627-1636.
Iefuji, H. et al., "Isolation and Characterization of a Yeast *Cryptococcus* sp. S-2 That Produces Raw Starch-digesting α-Amylase, Xylanase, and Polygalacturonase.", Biosci. Biotech. Biochem., Dec. 23, 1994, vol. 58, No. 12, pp. 2261-2262.
"Classification and Identification of Microbes", Tokyo University Press, pp. 92 to 93, Jun. 20, 1975; with partial English translation.
International Search Report dated Jul. 23, 2013, issued in corresponding application No. PCT/JP2013/061829.
Notification of Transmittal of Translation of the International Preliminary Report on Patentability (Chapter I or Chapter II) (Forms PCT/IB/338) of the International Application No. PCT/JP2013/061829 mailed Nov. 27, 2014 with Forms PCT/IB/373 and PCT/ISA/237. (5 pages).

* cited by examiner

*Primary Examiner* — Anne Gussow
*Assistant Examiner* — Mindy G Brown
(74) *Attorney, Agent, or Firm* — Westerman, Hattori, Daniels & Adrian, LLP

(57) ABSTRACT

The present invention provides a host for genetic recombination useful in the production of heterologous proteins in a large scale, by suppressing the production of extracellular polysaccharides in the basidiomycetous yeasts. *Cryptococcus* sp. S-2 D11 strain (FERM BP-11482) which is characterized in that the production of extracellular polysaccharides is suppressed as compared with the parent strain.

2 Claims, No Drawings

BASIDIOMYCETOUS YEAST MUTANT

TECHNICAL FIELD OF THE INVENTION

The present invention relates to a novel basidiomycetous yeast mutant wherein the production of extracellular polysaccharides causing a problem in a large-scale production of heterologous protein is greatly suppressed as compared with the existing basidiomycetous yeast.

BACKGROUND ART

As a result of development in gene recombination technology, it is now possible to manufacture industrially useful proteins in large amount utilizing prokaryotes and eukaryotes as hosts. As a host of prokaryote, bacterium such as *Escherichia coli* is commonly used while, as a host of eukaryote, yeast such as genus *Saccharomyces* or *Pichia pastris* is commonly used.

Since yeasts usually grow quickly, they can be cultured in higher cell density than bacteria. Further, in yeasts, separation of cells from culture liquid is easier than in bacteria whereby extracting and purifying steps of the produced protein can be made simpler. Therefore, yeasts have now been frequently used as the hosts for the production of useful proteins by means of gene recombination technology.

In view of usefulness of the yeasts as such, the Applicants have selected, from various yeasts, the *Cryptococcus* sp. S-2 strain [this is a kind of basidiomycetous yeast and has been internationally deposited on Sep. 5, 1995 under the accession number FERM BP-10961 at International Patent Organism Depositary of the National Institute of Advanced Industrial Science and Technology (current name: National Institute of Technology and Evaluation) located at Central No. 6, 1-1 Higashi 1-chome, Tsukuba-shi, Ibaraki-ken, Japan (Postal Code: 305-8566) (which has now been moved to Room 120, 2-5-8 Kazusa Kamatari, Kisarazu-shi, Chiba-ken, Japan (Postal Code: 292-0818)] exhibiting a characteristic of producing the proteins such as α-amylase, acidic xylanase and cutinase in large amount and of secreting them to the outside of cells (See Non-Patent Document 1).

The Applicants have further proposed the large-amount production of heterologous proteins other than the proteins which are inherently produced by the yeast, utilizing the high productivity of extracellular proteins by the above strain. Furthermore, in order to more efficiently select the transformant into which exogenous gene is introduced, they have proposed acquiring a uracil-requiring strain (U5 strain) from *Cryptococcus* sp. S-2 strain by means of spontaneous mutation (See Non-Patent Document 2).

As such, the basidiomycetous yeast such as *Cryptococcus* genus is very useful as a host for the production of heterologous protein by means of genetic recombination. However, the basidiomycetous yeast has such a problem that large amount of polysaccharides are produced outside the cells as shown in the Non-Patent Document 3. Since the extracellular production of polysaccharides as such raises the viscosity of the culture liquid, it is apt to cause insufficient separation and clogging of ultrafiltration membrane during the steps of cell removal from the culture liquid and of protein purification whereupon purification of proteins in high efficiency has been difficult.

In view of the above, there have been used up to now the methods such as (i) a method wherein the supernatant of the culture liquid is frozen and melted so that the extracellular polysaccharides are aggregated and removed, (ii) a method wherein cold acetone is added to the supernatant of the culture liquid to aggregate the extracellular polysaccharides followed by removing using a glass wool filter and (iii) a method wherein the extracellular polysaccharides are aggregated and precipitated using polyethylene glycol. However, any of those methods is not suitable for its scaling up in view of operability and economy. Thus, with regard to the method (i), there is a problem that freezing of the culture liquid is not easy in big scale. With regard to the method (ii), it is inefficient to pour large amount of acetone thereinto followed by evaporating, and a special consideration is needed for the safety. Further, with regard to the method (iii), there is a risk that the use of polyethylene glycol may deteriorate the ultrafiltration membrane which is used in the latter step and, in addition, there is a problem in the treatment of waste liquid.

Due to those reasons, it is difficult in view of operability, economy and safety to remove the polysaccharides which are produced and secreted in large amount outside the cells. Accordingly, there is a problem that the basidiomycetous yeast is not suitable as a host for the production of heterologous proteins in a large scale.

PRIOR ART DOCUMENTS

Non-Patent Documents

Non-Patent Document 1: Biosci. Biotech. Biochem., 58(12), 2261-2262, 1994

Non-Patent Document 2: Appl. Microbiol. Biotechnol. 2011 Nov. 15. (Construction of a new recombinant protein expression system in the basidiomycetous yeast *Cryptococcus* sp. strain S-2 and enhancement of the production of a cutinase-like enzyme.)

Non-Patent Document 3: Classification and Identification of Microbes (Tokyo University Press), pages 92 to 93

DISCLOSURE OF THE INVENTION

Problem that the Invention is to Solve

The present invention has been made for overcoming the problems as such in the prior art and its object is to provide a host for genetic recombination useful in the production of heterologous proteins in a large scale, by suppressing the production of extracellular polysaccharides in the basidiomycetous yeasts.

Means for Solving the Problem

The present inventors have earnestly conducted the investigations for achieving the object as such and, as a result thereof, they have isolated a UV mutant from *Cryptococcus* sp. S-2 strain (being classified as genus *Cryptococcus* which is a kind of basidiomycetous yeast) and have succeeded in obtaining a mutant strain wherein the productivity of extracellular polysaccharides by this microbe is greatly reduced as compared with the parent strain.

The present invention has been accomplished on the basis of those findings and is constituted from the following (1) to (2):

(1) *Cryptococcus* sp. S-2 D11 strain (FERM BP-11482) which is characterized in that the production of extracellular polysaccharides is suppressed as compared with the parent strain.

(2) A method for producing a target protein, characterized in that it comprises a step of transforming a gene of the target protein to the strain mentioned in (1), a step of culturing the resulting transformant, and a step of collecting the target protein from the resulting culture product.

Advantages of the Invention

In the mutant strain of the present invention, production of extracellular protein inhibiting the separation and purification of protein is greatly suppressed as compared with the parent strain whereby insufficient separation of protein and clogging of ultrafiltration membrane hardly happen and, even when it is used as a host for a recombination production of heterologous protein in large scale, protein can be efficiently purified.

BEST MODE FOR CARRYING OUT THE INVENTION

The mutant strain of the present invention is obtained by UV mutagenesis from the basidiomycetous yeast of genus Cryptococcus and has such a characteristic that the production of extracellular polysaccharides is greatly suppressed as compared with the conventional strain. As a result, viscosity of the culture liquid does not significantly rise by the polysaccharides and said strain is very suitable as a host for the production of heterologous protein in a large scale.

The parent strain for the mutant strain of the present invention is a strain which is obtained from Cryptococcus sp. S-2 strain (which has been internationally deposited on Sep. 5, 1995 under the accession number FERM BP-10961 at International Patent Organism Depositary of the National Institute of Advanced Industrial Science and Technology) by means of spontaneous mutation and molecular biological mutagenesis. To be more specific, the parent strain for the mutant strain of the present invention is such a strain wherein uracil-requiring strain (U5 strain) obtained by spontaneous mutation of Cryptococcus sp. S-2 strain by means of UV irradiation is subjected to a molecular biological means to destroy the specific gene (Ade 1 gene coding for phosphoribosyl-aminoimidazole synthetase) so as to make uracil- and adenine-requiring. Cryptococcus sp. S-2 strain is a strain which is expected to exhibit an ability to produce heterologous protein in large amount and to secrete it to the outside of the cells. Since the parent strain for the mutant of the present invention has a uracil- and adenine-requiring property in addition to the above-mentioned useful characteristic of Cryptococcus sp. S-2 strain, selection of a transformant into which exogenous gene is introduced can be carried out efficiently.

As shown in Examples, the mutant strain of the present invention was selected by such a way that a parent strain thereof is subjected to UV mutagenesis and the polysaccharide production amount, etc. of the resulting various mutants are measured and compared with the parent strain. It has a characteristic that the production of extracellular polysaccharide is significantly suppressed as compared with the parent strain.

Although the reason why the production of the extracellular polysaccharides is suppressed in the mutant strain of the present invention has not been so clear yet, it is likely that some mutation is introduced into the gene which is related to the extracellular polysaccharide production of the parent strain or that expression of the gene which is related to the extracellular polysaccharide production is suppressed due to some way.

The strain of the present invention has been internationally deposited on Mar. 23, 2012 under the accession number FERM BP-11482 at International Patent Organism Depositary of the National Institute of Technology and Evaluation located at Central No. 6, 1-1 Higashi 1-chome, Tsukuba-shi, Ibaraki-ken, Japan (Postal Code: 305-8566) (which has now been moved to Room 120, 2-5-8 Kazusa Kamatari, Kisarazu-shi, Chiba-ken, Japan (Postal Code: 292-0818).

Mycological properties of the mutant of the present invention are thought to be identical with those of Cryptococcus sp. S-2 wherefrom the mutant is derived and are as shown in the following Table 1.

TABLE 1

| Fermentation | − |
|---|---|
| Color test with Diazonium Blue (DBB) | + |
| Production of ammonia from urea | + |
| Secretion of DNase | + |
| Contents of G + C in nucleic acid DNA | 67 molar % |
| Main ubiquinone | Q-10 |

| Anabolism of carbon compounds: | | | |
|---|---|---|---|
| D-Glucose | + | D-Galactose | + |
| L-Sorbose | − | D-Glucosamine | − |
| D-Ribose | + | D-Xylose | + |
| L-Arabinose | + | D-Arabinose | W |
| L-Rhamnose | + | Sucrose | + |
| Maltose | + | Trehalose | + |
| Lactose | + | Raffinose | + |
| Cellobiose | + | Melibiose | + |
| Inulin | W | Starch | + |
| Erythritol | + | Glycerol | − |
| Ribitol | W | Xylitol | + |
| D-Glucuronic acid | + | Inositol | + |
| Citric acid | W | Ethanol | − |

| Anabolism of nitrogen compounds: | | | |
|---|---|---|---|
| Nitrate | − | Ethylamine | − |
| Cadaverine | W | Glucosamine | − |
| Formation of starch | | | − |
| Growth at 37° C. | | | − |

Note)
In the table, + means positive, − means negative and W means weak.

A culturing method for the mutant strain of the present invention is the same as that for Cryptococcus sp. S-2 strain wherefrom the mutant strain was derived. For example, it can be cultured in the YM medium mentioned in Example under the condition of about 20 to 25° C. and about pH 3.0 to 9.0.

The mutant strain of the present invention can be advantageously utilized as a host for the recombination production of heterologous protein, particularly for the recombination production in large scale, utilizing the characteristic that production of extracellular polysaccharides is suppressed. Thus, according to the present invention, there is provided a method for the production of a target protein, characterized in that it comprises a step of transforming a gene of the target protein to the mutant strain of the present invention, a step of culturing the resulting transformant, and a step of collecting the target protein from the resulting culture product.

Transformation of the gene of a target protein to the mutant strain of the present invention can be carried out according to the conventional method. Culture of the resulting transformant can be carried out using the same medium and culturing condition as those for the strain before the transformation. During the culture, the transformant expresses the gene of the integrated target protein, produces a target protein, and secretes it to the outside of the cells. Although the culturing time may be different more or less depending upon the condition, the culture may be finished within an appropriate period by checking the time when the protein production reaches the highest yield and it is usually about 60 to 120 hours. After the culture, a target protein can be collected from the resulting culture product according to the conventional method. When the mutant strain of the present invention is used as a host, secreted amount of the extracellular saccharides is significantly small whereby viscosity of the cultured product does not rise and separation and purification of the target protein can be carried out easily and efficiently even if it is in a large scale.

EXAMPLES

The present invention will now be specifically illustrated by way of the following Examples although the present invention is not limited thereto. Incidentally, "%" in Examples stands for "% by weight" unless otherwise mentioned.

1. UV Mutation Treatment of *Cryptococcus* Sp. S-2 Strain

*Cryptococcus* sp. S-2 A1U5 strain [a uracil- and adenine-requiring strain prepared by subjecting the uracil-requiring strain (U5 strain) shown in Non-Patent Document 3 to a molecular biological means to destroy Ade 1 gene coding for phosphoribosyl-aminoimidazole synthetase] was used as a parent strain. A mutant is generated by a UV mutation treatment of this strain. To be more specific, cells of this strain in a platinum loop were planted on a YM medium [comprising 0.3% of yeast extract (manufactured by Difco), 0.3% of malt extract (manufactured by Difco), 0.5% of peptone (manufactured by Difco) and 1.0% of glucose (manufactured by Nacarai Tesque)] and subjected to a shake culture at 25° C. for two days. After that, the culture liquid was subjected to a stepwise dilution with sterile water and 0.1 ml of the diluted culture liquid was planted to a YM agar medium [comprising 0.3% of yeast extract (manufactured by Difco), 0.3% of malt extract (manufactured by Difco), 0.5% of peptone (manufactured by Difco), 1.0% of glucose (manufactured by Nacarai Tesque), and 1.5% of agar powder (manufactured by Nacarai Tesque)] by smearing. This planted medium was placed at the position of about 30 cm apart from the light source of a sterilizing light GL-15 (manufactured by Panasonic Corporation), irradiated with UV for 10 minutes and then subjected to a stationary culture at 25° C. for three days. The grown strain was subcultured to give about 500 colonies of the mutant strain.

2. Selection of UV Mutant Strain of *Cryptococcus* Sp. S-2 Strain

The mutant strain (about 500 colonies) was planted to a YX medium [2% of yeast extract (manufactured by Difco), 5% of Xylose (manufactured by Nacarai Tesque)] and subjected to a shake culture at 25° C. for three days. To 0.5 ml of the supernatant of the culture liquid was added 5 ml of cold ethanol so that the extracellular polysaccharides were precipitated. Four colonies of the strain (D1 strain, D9 strain, D10 strain, and D11 strain), the precipitated amount of which was reduced as compared with the parent strain, were selected. In the above, D11 strain is the mutant strain of the present invention. After that, the selected 4 colonies and the parent strain (A1U5 strain) were added to 100 ml of a culture liquid [5% of yeast extract (manufactured by Difco), 50% of Xylose (3 ml/L/hour)] and subjected to a stirring culture for 3 days. After the culture, amount of the produced extracellular polysaccharides, amount of the produced xylanase and amount of the cells were measured for each of them according to the following procedures.

Amount of the Produced Extracellular Polysaccharides

To 0.5 ml of the supernatant obtained by centrifugal separation of the culture liquid after the culture was added 5 ml of cold ethanol so that the extracellular polysaccharides were precipitated. After removing the supernatant obtained by centrifugal separation, the precipitate was dissolved in 10 ml of distilled water. The resulting solution was used for the measurement of the saccharide content per protein by a phenol sulfate method. To be more specific, 0.5 ml of a dissolving liquid, 0.5 ml of 5% (w/v) phenol solution and 2.5 ml of 97% sulfuric acid were mixed with each other and cooled down to room temperature and the absorbance at 490 nm was measured. A calibration curve was prepared using 0 to 200 mg/L of D-mannose standard solutions to estimate the saccharide content in the solution whereupon the saccharide content in the culture liquid was calculated.

Amount of the Produced Xylanase

SDS-PAGE analysis was conducted using a supernatant obtained by centrifugal separation of the culture liquid after the culture and the amount of the produced xylanase was confirmed. As to a kit for the SDS-PAGE, Nu-PAGE 4-12% Bis-Tris Gel (manufacture by Invitrogen) was used and the band intensity of a band for xylanase appearing at the position of about 20 kDa was calculated by Gel-pro Analyzer (manufacture by Nippon Roper) and was adopted as the amount of the produced xylanase.

Amount of the Cells

Absorbance of the culture liquid at 660 nm after the culture was measured using a spectrophotometer and adopted as the amount of the cells.

Result of comparison of amount of the produced extracellular polysaccharides, amount of the produced xylanase and amount of the cells in each of the strains is shown in Table 2.

TABLE 2

|  | Amount of the produced extracellular polysaccharides (g/L) | Amount of the produced xylanase (Mass) | Amount of the cells (OD660Abs) |
| --- | --- | --- | --- |
| A1U5 strain | 4.85 | 17.3 | 129.1 |
| D1 strain | 1.60 | 8.5 | 136.5 |
| D9 strain | 1.67 | 13.7 | 153.0 |
| D10 strain | 1.89 | 10.2 | 72.1 |
| D11 strain | 1.20 | 16.8 | 124.6 |

As shown in Table 2, A1U5 strain (a parent strain) produced 4.85 g/L of extracellular polysaccharides while the amount of the produced extracellular polysaccharides by D11 strain was 1.20 g/L. As such, the extracellular polysaccharide production by D11 strain was greatly suppressed (to an extent of about 25%) as compared with the parent strain. Incidentally, amount of the produced xylanase and amount of the cells in the case of D11 strain were nearly the same as those of the parent strain. In the mutant strains other than D11 strain, degree of suppression for the production of extracellular polysaccharides was inferior to D11 strain and the production amount of xylanase was also inferior to the parent strain. Moreover, D10 strain was inferior not only in terms of the production amounts of extracellular polysaccharides and xylanase but also in terms of the amount of the cells.

It is noted from the above results that the D11 strain is such a mutant strain wherein the production of extracellular polysaccharides which disturbs the separation and purification of protein is significantly suppressed and that the D11 strain exhibits the same growing ability for the cells and the same productivity for the extracellular proteins as in the case of the parent strain. Accordingly, it is believed that the D11 strain is very useful as an expression host for the large-scale production of heterologous protein.

INDUSTRIAL APPLICABILITY

The *Cryptococcus* sp. S2 mutant strain of the present invention is a mutant wherein the production of extracellular polysaccharides is greatly suppressed as compared with the parent strain whereby there is no increase in the viscosity of a culture liquid due to the extracellular polysaccharides and, even when heterologous protein is produced in a large scale, the steps for removal of cells from the culture liquid and for purification of the protein can be efficiently carried out. Accordingly, the mutant strain according to the present invention is very useful as an expression host when heterologous protein is produced in a large scale.

The invention claimed is:

1. A *Cryptococcus* strain deposited as FERM BP-11482.
2. A method for producing a target protein, comprising:
    transforming a gene of the target protein to a *Cryptococcus* strain deposited as FERM BP-11482,
    culturing the resulting transformant, and
    collecting the target protein from the resulting culture product.

* * * * *